US00PP29450P2

(12) United States Plant Patent
Van Swieten

(10) Patent No.: US PP29,450 P2
(45) Date of Patent: Jul. 3, 2018

(54) *PHALAENOPSIS* ORCHID PLANT NAMED 'PHALFUXE'

(50) Latin Name: ***Phalaenopsis* hybrid**
Varietal Denomination: PHALFUXE

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,836

(22) Filed: Mar. 6, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

UPOV hit on *Phalaenopsis* plant named 'Phalfuxe', QZ PBR 20162208, Sep. 13, 2016.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFUXE', particularly characterized by having large, yellow, spotted flowers, 1 to 2 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALFUXE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUXE'.

The new *Phalaenopsis* plant is a product of a planned breeding program conducted by the inventor in Bleiswijk, The Netherlands. The objective of this breeding program was to create a new *Phalaenopsis* plant with large, yellow, spotted flowers, suitable for potted plant production.

The new *Phalaenopsis* plant 'PHALFUXE' is a result of cross-pollination made by the inventor in March 2008 in Bleiswijk, The Netherlands of the proprietary female, or seed parent, *Phalaenopsis* hybrid '11301-05' (unpatented) with the proprietary male, or pollen parent, *Phalaenopsis* hybrid '01-1849' (unpatented).

The new *Phalaenopsis* was selected by the inventor as a single plant within the progeny of the stated cross-pollination in a controlled greenhouse in Bleiswijk, The Netherlands in January 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFUXE' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUXE' as a new and distinct variety of *Phalaenopsis* plant.

1) Large, yellow, spotted flowers;
2) 1 to 2 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in January 2017. Colors in the photographs may differ from the color values cited in the detailed botanical description, which accurately describe the actual colors of the new variety.

Figure 1:
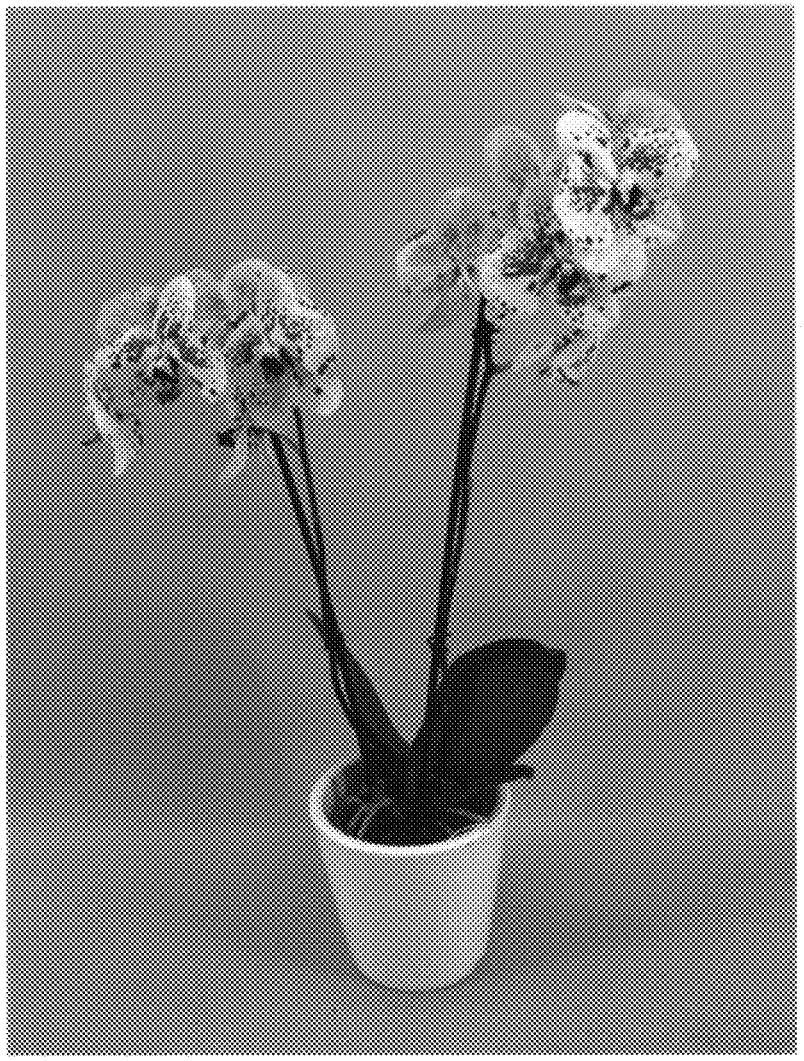
FIG. 1 shows the overall plant habit, including blooms and foliage of 'PHALFUXE'.
Figure 2:
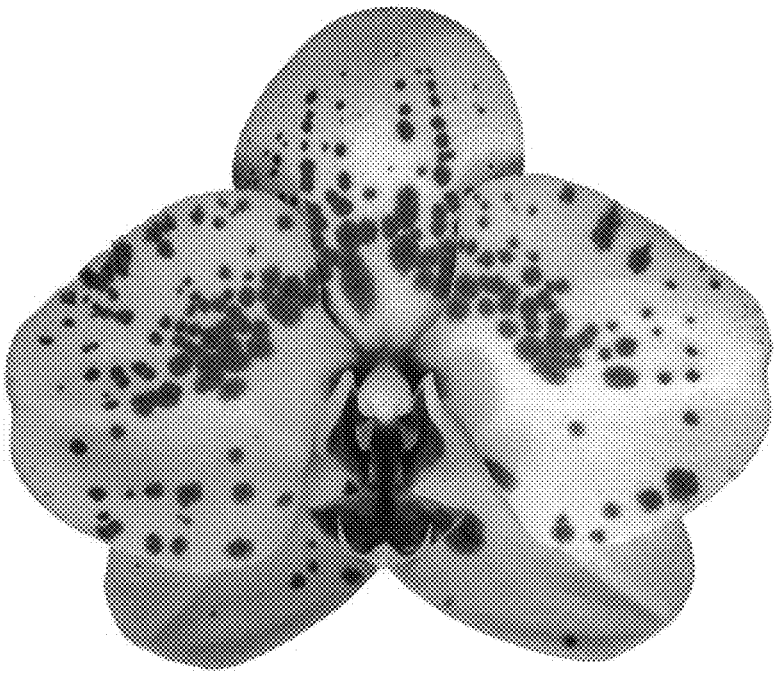
FIG. 2 shows a close-up of a flower of 'PHALFUXE'.
Figure 3:
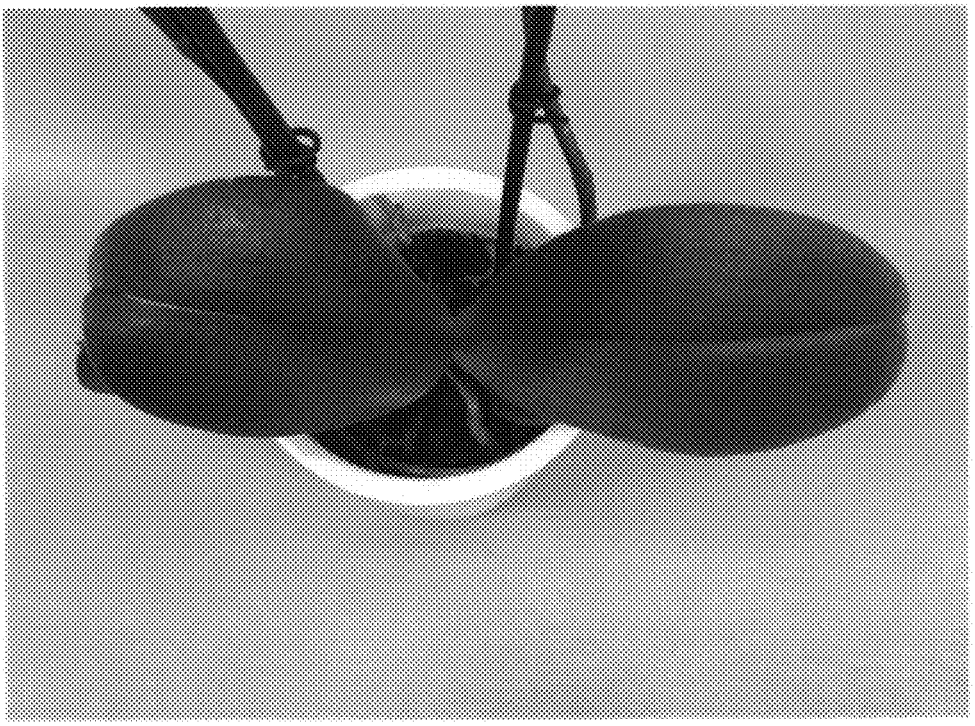

FTG. 3 shows a close-up of the leaves of 'PHALFUXE'.

DESCRIPTION OF THE NEW VARIETY

The following detailed description sets forth the distinctive characteristics of 'PHALFUXE'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUXE'.

Parentage:

*Female parent*.—*Phalaenopsis* cultivar '11301-05' (unpatented).

*Male parent*.—*Phalaenopsis* cultivar '01-1849' (unpatented).

Propagation:

*Type*.—Meristem tissue culture.

Roots:

*Root description*.—Greyed-green colored roots (RHS 190A/B) with branching lateral roots having light green colored root tips (RHS 146D).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 44.0 cm to 54.0 cm.

*Width* (*measured from leaf tips*).—About 23.0 cm to 28.0 cm.

*Vigor*.—Strong.

Leaves:

*Mature leaves*.—Quantity per plant: 6 to 8 leaves are produced before flowering. Length (fully expanded): 13.0 cm to 16.0 cm. Width: 7.5 cm to 8.5 cm. Shape: Obovate. Base shape: Slightly elongated. Apex: Unequal rounded. Leaf blade angle with the petiole (measured from the horizontal position): Between 25 degrees and 40 degrees. Leaf margin: Entire. Color: Upper surface: RHS 147A. Lower surface: RHS 147B. Texture: Smooth. Thickness: 2.5 mm to 2.8 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—8 to 12.

*Length*.—44.0 cm to 54.0 cm.

*Diameter*.—4.8 mm to 5.0 mm.

*Strength*.—Strong.

*Aspect*.—Upright to slightly pendant.

*Texture*.—Smooth.

*Color*.—Green (RHS 146A) with a touch of brown (RHS 200B).

*Internode length*.—35.0 mm to 40.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 92.0 mm to 97.0 mm.

*Flowering time*.—First flowers can be expected 10 to 11 months after planting in a 12 cm (diameter) pot.

*Flower*.—Height: 87.0 mm to 92.0 mm. Diameter: 95.0 mm to 100.0 mm. Depth of lip: 18.0 mm to 20.0 mm.

*Flower longevity*.—On the plant: 16 to 21 weeks.

*Fragrance*.—Absent.

*Flower bud*.—Average size: Medium. Length: 19.0 mm to 21.0 mm. Width: 16.0 mm to 18.0 mm. Shape: Egg shaped. Color: Green (RHS 144B) with diluting spots (RHS N79B).

*Petals*.—Arrangement: Open/free. Shape: Semi-circular. Apex: Emarginated asymmetric. Margin: Slightly undulated. Length (from base to tip): 41.0 mm to 43.0 mm. Width: 50.0 mm to 52.0 mm. Color (when fully opened): Upper surface: Basic color: Yellow (RHS 1D). Over color: Dark red-purple spots (RHS N79C). Lower surface: Basic color: Yellow (RHS 1D). Over color: Diluting dark red-purple spots (RHS N79B).

*Dorsal sepal*.—Shape: Broad elliptic. Apex: Rounded symmetric. Margin: Entire. Length (from base to tip): 46.0 mm to 48.0 mm. Width: 37.0 mm to 39.0 mm. Color (when fully opened): Upper surface: Basic color: Yellow (RHS 1D). Over color: Dark red-purple spots (RHS N79C). Lower surface: Basic color: Yellow (RHS 1D). Over color: Diluting dark red-purple spots (RHS N79B); green-yellow in the middle (RHS 145C).

*Lateral sepals*.—Shape: Ovate. Apex: Obtuse asymmetric. Margin: Entire. Length (from base to tip): 45.0 mm to 47.0 mm. Width: 31.0 mm to 33.0 mm. Color (when fully opened): Upper surface: Basic color: Yellow (RHS 1D). Over color: Dark red-purple spots (RHS N79C). Lower surface: Basic color: Green-yellow (RHS 145C). Over color: Diluting dark red-purple spots (RHS N79B).

*Labellum* (*lip*).—Whiskers: Present. Length of whiskers: 4.0 mm to 6.0 mm. Color of whiskers: Light yellow (RHS 160B). Pubescence on the lip: Absent.

*Lateral lobe*.—Shape: Weakly spatulate. Margin: Entire. Length: 15.0 mm to 17.0 mm. Width: 9.0 mm to 11.0 mm. Color: Dark red at the base (RHS 187A); white on one side (RHS NN155C) and yellow on the other side (RHS 6A).

*Apical lobe*.—Shape: Trullate. Margin: Entire. Length: 19.0 mm to 21.0 mm. Width: 18.0 mm to 20.0 mm. Color: Yellow edge (RHS 2B) toward the callus; dark red spots (RHS 187A/B) and light yellow (RHS 160B) toward the whiskers.

*Callus*.—Average size: Medium. Height: 0.5 cm to 0.7 cm. Length: 0.4 cm to 0.6 cm. Width: 0.3 cm to 0.5 cm. Color: Dark red (RHS 187A).

Reproductive organs:

*Column*.—Length: 9.0 mm to 11.0 mm. Diameter: 5.4 mm to 5.6 mm. Color: Dark red at the base (RHS N79C); white toward the tip (RHS NN155C).

*Pollinia*.—Quantity: 2. Diameter: 1.0 mm to 1.2 mm. Color: Yellow-orange (RHS 24B).

*Ovary*.—Length: 10.0 mm to 12.0 mm. Diameter: 2.4 mm to 2.6 mm.

*Pedicel*.—Length: 41.0 mm to 43.0 mm. Diameter: 3.1 mm to 3.3 mm. Color: Green (RHS 144C) to light pink/white (RHS N155C).

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALFUXE' differs from female parent plant '11301-05' (unpatented) in that 'PHALFUXE' has a medium sized callus, yellow (RHS 1D) flowers with trullate apical lobes, and weakly spatulate lateral lobes, whereas '11301-05' has a small callus, yellow (RHS 6B) flowers with rhombic apical lobes, and oblong lateral lobes. Additionally, 'PHALFUXE' has larger flowers and longer whiskers than '11301-05'.

'PHALFUXE' differs from male parent plant '01-1849' (unpatented) in that 'PHALFUXE' has a medium sized callus, yellow flowers with spots, trullate apical lobes and weakly spatulate lateral lobes, whereas '01-1849' has a large callus, white flowers, triangular apical lobes and spatulate lateral lobes. Additionally, 'PHALFUXE' has smaller flowers and much shorter whiskers than '01-1849'.

'PHALFUXE' is most similar to the commercial *Phalaenopsis* plants named 'PHALDEMFOP' (unpatented) and 'PHALDRYLO' (unpatented). 'PHALFUXE' differs from the commercial variety 'PHALDEMFOP' in that 'PHALFUXE' has an apical lobe with dark red spots, yellow edge toward the callus and light yellow toward the whiskers, and leaves without anthocyanin coloration and a rounded apex, whereas 'PHALDEMFOP' has an apical lobe that is purple and red-brown toward the whiskers and spotted at the base, and leaves with anthocyanin coloration and an obtuse apex. Additionally, 'PHALFUXE' has larger flowers than 'PHALDEMFOP'.

'PHALFUXE' differs from the commercial variety 'PHALDRYLO' in that 'PHALFUXE' has an apical lobe with dark red spots (RHS 187A/B), yellow (RHS 2B) edge toward the callus and light yellow (RHS 160B) toward the whiskers, whereas 'PHALDRYLO' has a yellow (RHS 7A) apical lobe with dark red spots (RHS 187C) and white (RHS NN155C) toward the whiskers. Additionally, 'PHALFUXE' has leaves without anthocyanin coloration and a rounded apex, whereas 'PHALDRYLO' has leaves with anthocyanin coloration and an obtuse apex.

I claim:

1. A new and distinct variety of *Phalaenopsis* plant named 'PHALFUXE', substantially as described and illustrated herein.

* * * * *